(12) United States Patent
Giese et al.

(10) Patent No.: US 8,144,904 B2
(45) Date of Patent: Mar. 27, 2012

(54) METHOD FOR GENERATING AN INDIVIDUAL HEARING DEVICE PROGRAM

(75) Inventors: Ulrich Giese, Erlangen (DE); Esfandiar Grafenberg, Effeltrich (DE)

(73) Assignee: Siemens Audiologische Technik GmbH, Erlangen (DE)

( * ) Notice: Subject to any disclaimer, the term of this patent is extended or adjusted under 35 U.S.C. 154(b) by 1321 days.

(21) Appl. No.: 11/810,977

(22) Filed: Jun. 7, 2007

(65) Prior Publication Data
US 2007/0299654 A1 Dec. 27, 2007

(30) Foreign Application Priority Data

Jun. 7, 2006 (DE) .......................... 10 2006 026 489

(51) Int. Cl.
*H04R 25/00* (2006.01)
*H04R 29/00* (2006.01)
(52) U.S. Cl. ........... 381/320; 381/60; 381/312; 381/314
(58) Field of Classification Search .................... 381/60, 381/312–331
See application file for complete search history.

(56) References Cited

U.S. PATENT DOCUMENTS
7,349,549 B2 * 3/2008 Bachler et al. ................ 381/314

FOREIGN PATENT DOCUMENTS
DE    199 28 115 A1    6/1999
EP    772374    *    7/1997
EP    1 320 282 A2    6/2003

* cited by examiner

*Primary Examiner* — Davetta W Goins
*Assistant Examiner* — Matthew Eason

(57) ABSTRACT

Sound quality and speech comprehensibility are to be improved for hearing device wearers when watching television. Provision is made for this purpose to record acoustic signals at a recording site on a data medium. The acoustic signals are recorded simultaneously with a first microphone as a first recording. The data medium is played back on an individual playback device in an individual environment. Here the signal played back from the data medium is re-recorded as a second recording with a second microphone. The two recordings are connected to each other, subtracted in particular, and the result is used to adjust a hearing device program. It is thus possible to take into account individual acoustic environmental conditions in the hearing device program.

20 Claims, 1 Drawing Sheet

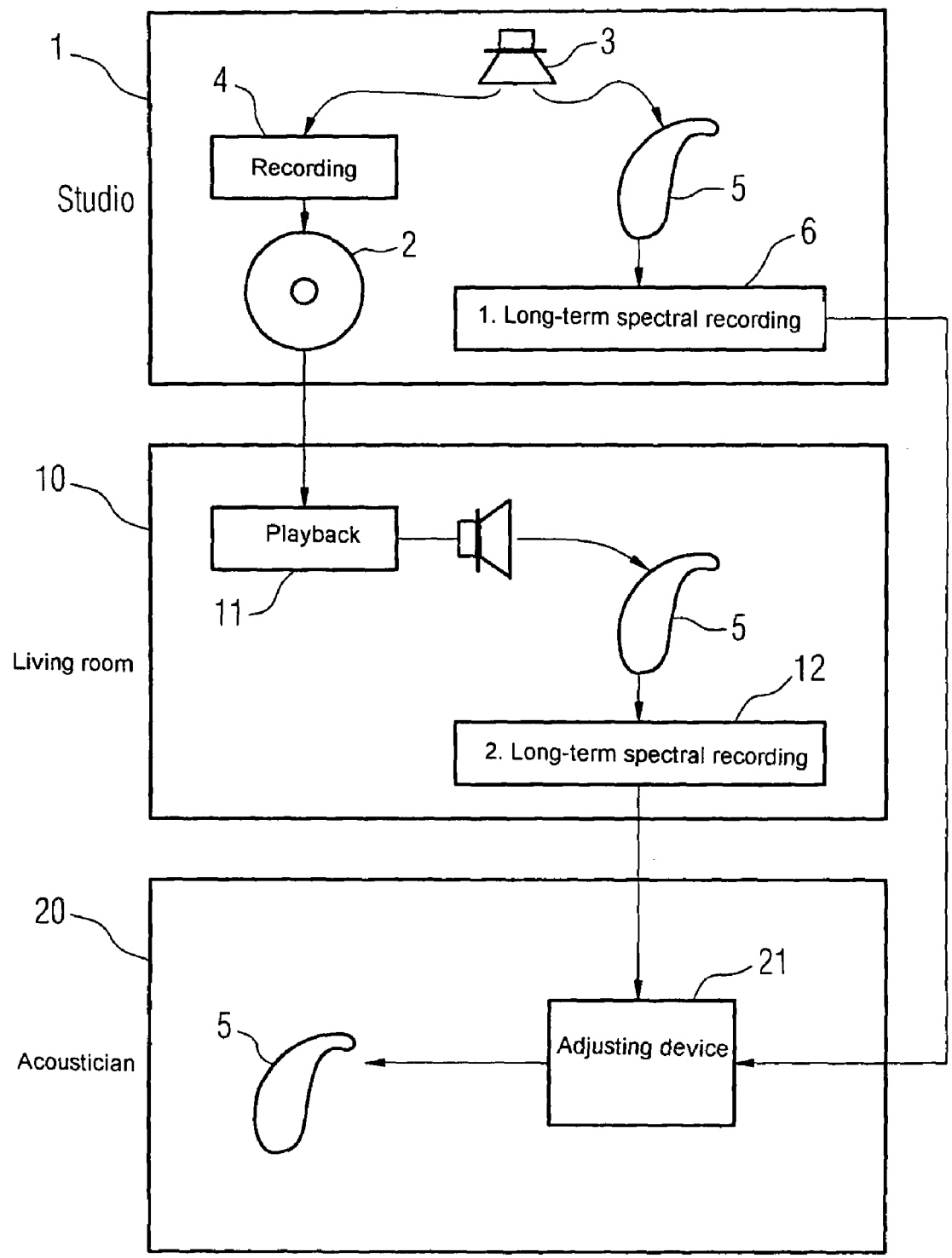

METHOD FOR GENERATING AN INDIVIDUAL HEARING DEVICE PROGRAM

CROSS REFERENCE TO RELATED APPLICATIONS

This application claims priority of German application No. 10 2006 026 489.4 filed Jun. 7, 2006, which is incorporated by reference herein in its entirety.

FIELD OF THE INVENTION

The present invention relates to a method for generating an individual hearing device program in order to improve sound quality and speech comprehensibility.

BACKGROUND OF THE INVENTION

Studies have demonstrated that speech comprehensibility and sound quality are frequently unsatisfactory for hearing device wearers when watching television. The reason for this is that the hearing device programs are generally only configured very broadly for the hearing situation "television" and therefore cannot cater to individual hearing situations. On the other hand hearing losses experienced by hearing device wearers are so diverse that individualization is not possible in this respect in terms of the speech comprehensibility of television programs. However the hearing situation "television" is regarded by hearing device wearers as highly important.

Practically every hearing device manufacturer currently offers a hearing device signal processing program for viewing television programs. In terms of their frequency response these hearing device programs are broadly rather different to other hearing device programs. However, the result in many cases is inadequate sound quality and speech comprehensibility.

A method for recording information in a hearing device is known from the publication EP 1 320 282 A2. This method is advantageous to the developer of hearing devices in that the selection of automatic operating settings can be tested and controlled as a function of the actual acoustic environments.

The publication DE 199 28 115 A1 further describes a method for adjusting hearing device parameters. An audio recording device is used here to record different audio information in different situations, which is subsequently used to adjust the hearing device.

SUMMARY OF THE INVENTION

The object of the present invention therefore consists in specifying a method with which it is possible to adjust hearing devices such that speech comprehensibility and sound quality are improved for media playback.

This object is inventively achieved by a method for generating an individual hearing device program by recording acoustic signals at a recording site as a basic recording on a data medium, by simultaneously recording the acoustic signals as a first recording with a first microphone at the recording site independently of the basic recording, by playing back the data medium on an individual playback device and/or in a predetermined individual environment that is different to the recording site, by re-recording as a second recording with a second microphone the signal played back by the data medium, by establishing a connection between the first recording and the second recording, and by adjusting a hearing device program as a function of the connection.

According to the invention sound quality and speech comprehensibility for media playback can thus be improved individually, since individual conditions can be taken into account with the adjustment of the hearing device.

The media production is preferably a film or video recording. Recording can then take place live in a studio, with the acoustic signals also being recorded simultaneously with the first microphone live in the studio.

The data medium can be a DVD that is played back with an individual television receiver as an individual playback device. Other storage media such as CDs, hard disks, tapes, etc. may of course also be used as data media for playback on an individual television receiver.

It is particularly advantageous if the first microphone and the second microphone are one and the same or an identical hearing device microphone. In this way the precise difference for a hearing device wearer between the acoustic situation in a studio and the individual acoustic situation, for example in a living room, can be determined and taken into account.

In accordance with a development of the inventive method the first and the second recording are both long-term spectral recordings. Thus the acoustic conditions during recording and playback can be generally assessed better.

A dereverberation algorithm of the hearing device program can be furthermore individually parameterized as a function of the connection. In this way it is possible to cater specifically to the reverberation characteristics of a hearing device wearer's environment when generating an individual hearing device program.

It is furthermore preferably possible to provide for an interface via which the connection data can be input directly into a hearing device. Thus for example filters in a hearing device can be configured very quickly.

The connection between the first and the second recording can be a quotient or difference between the two recordings. However prudent alternative mathematical connections may also be used in order to take account of the difference between a standard hearing situation and an individual hearing situation for hearing device playback.

BRIEF DESCRIPTION OF THE DRAWING

The present invention is now described in more detail with reference to the appended drawing, which shows a basic sketch of an exemplary embodiment of a method according to the invention.

DETAILED DESCRIPTION OF THE INVENTION

The exemplary embodiments shown in more detail below represent preferred embodiments of the present invention.

The hearing device program for television is to be individually adjusted for a hearing device wearer. To this end, a recording of a television program is first made in a standard acoustic situation in a studio 1 on a data medium, in particular a DVD 2. The signal source is symbolized here by a loudspeaker 3 that generates the sound for a recording device 4. The recording device 4 then supplies the DVD 2.

At the same time the acoustic output signals from the loudspeaker 3 in the studio 1 are captured by means of a hearing device 5. During this process the hearing device 5 is situated on an artificial head, and specifically in the vicinity of the temple, where it would generally also be worn by the hearing device wearer. Thus the acoustic environmental conditions correspond approximately to the actual conditions that would be encountered by a hearing device wearer.

A statistical average of the recording captured by means of the hearing device 5 is obtained, which results in a first long-term spectral recording 6. This reflects the acoustic environment in the studio 1 during the recording.

The DVD 2 is now played back in the living room 10 of a hearing device wearer. The living room 10 here represents an individual acoustic environment, which can in principle also be any other room or also a set of headphones. The important factor is that the playback takes place via an individual device belonging to the hearing device wearer at the usual volume level in their familiar environment. The playback device 11 is specifically the individual television set, which reproduces an acoustic output signal in the living room 10 that corresponds to the recording on the DVD 2.

The hearing device wearer will typically always view television programs from a certain location in his living room 10. His ear is then positioned at a particular specified location. During playback of the DVD 2 the sound is re-recorded at this location by means of the same microphone, in this case the hearing device microphone. For this purpose, a loan hearing device can be used by an acoustician, the built-in microphone can be used in a remote controller or a hearing device microphone can be used directly.

The recording performed again using this microphone or the hearing device 5 mirrors the effects of the individual television set and the acoustic properties of the hearing device wearer's television room or living room. This re-recording takes place for example digitally in MP3 format. In addition to the playback of the film or video on the DVD 2, other defined test signals can also be played back in the living room 10 or in the individual environment and accordingly re-re-corded by means of the hearing device 5 or another microphone. A second long-term spectral recording 12 is generated from these recordings performed in the living room 10, in a similar manner to that produced from the recordings performed in the studio 1.

Both the long-term spectral recordings 6 and 12 are now communicated to an acoustician 20. Communication can also take place for example via a data network or online as the case may be. Using an adjusting device 21 the acoustician subtracts from one another the two long-term spectral recordings, one originating live and one from the hearing device wearer's television set, in order also to obtain data about the hearing device wearer's acoustic situation in his usual environment. Based on these data the frequency response of the hearing device 5 is adjusted individually in the hearing device program optimized for television viewing. Individual adjustment parameters for dereverberation algorithms can additionally be extracted from the recording of special test signals.

For the adjustment the acoustician inputs the data into the software as for an RECD (Real Ear to Coupler Difference), with which it is possible using current software to adjust the frequency response to the size of the auditory canal (e.g. for children). However the data can also be supplied automatically for example via a USB connection. Adjusting the hearing device individually in this manner then improves sound quality and speech comprehensibility for the hearing device wearer when watching television.

The invention claimed is:

1. A method for generating an individual hearing aid device program optimized for media playback, comprising:
    recording a first acoustic signal as a first recording with a first hearing aid device microphone while the first acoustic signal is played at a first recording site from an individual playback device, simultaneously with and independently of the first recording, recording a basic recording of the first acoustic signal on to a data medium, wherein the first recording captures acoustic environmental conditions of the first recording site as a first spectral recording;
    recording a second acoustic signal while playing back the basic recording stored on the data medium on an individual playback device at a second recording site as a second recording with a second hearing aid device microphone of a second hearing aid device, wherein the second recording captures acoustic environmental conditions of the second recording site as a second spectral recording;
    receiving and comparing by an adjusting device the first and the second spectral recordings to determine a connection data between the acoustic environmental conditions of the second recording site compared to the acoustic environmental conditions of the first recording site; and
    adjusting an individual hearing aid device program of the second hearing aid device as a function of the connection data.

2. The method as claimed in claim 1, wherein the first and the second acoustic signals are signals from a film or a video recording.

3. The method as claimed in claim 1, wherein the individual playback device is an individual television receiver located at the second recording site.

4. The method as claimed in claim 1, wherein the first and the second hearing aid microphones are identical.

5. The method as claimed in claim 1, wherein the first and the second recordings are long-term spectral recordings.

6. The method as claimed in claim 1, wherein a dereverberation algorithm of the program for the second hearing aid device is individually parameterized based on the connection data.

7. The method as claimed in claim 1, wherein the connection data is directly inputted into the second hearing aid device via an interface.

8. The method as claimed in claim 1, wherein the connection data is a quotient or a difference between the first and the second recordings.

9. The method as claimed in claim 1, wherein the data medium is played back in a predetermined individual environment that is different from the first recording site.

10. The method as claimed in claim 9, wherein the predetermined individual environment is a place where a wearer of the second hearing aid device usually listens to the playing back.

11. A system for generating an individual hearing aid device program optimized for media playback, comprising:
    a first hearing aid device microphone that records a first acoustic signal as a first recording while the first acoustic signal is played at a first recording site from an individual playback device, simultaneously with and independently of the first recording, recording a basic recording of the first acoustic signal on to a data medium, wherein the first recording captures acoustic environmental conditions of the first recording site as a first spectral recording;
    a second hearing aid device microphone of a second hearing aid device that records a second acoustic signal as a second recording that is played by an individual playback device that plays back the data medium at a second recording site, wherein the second recording captures acoustic environmental conditions of the second recording site as a second spectral recording; and
    an adjusting device for receiving and comparing the first and the second spectral recordings to determine a connection data between the acoustic environmental conditions of the second recording site compared to the acoustic environmental conditions of the first recording site, and for adjusting an individual hearing aid device program of the second hearing aid device as a function of the connection data.

12. The system as claimed in claim 11, wherein the first and the second acoustic signals are signals from a film or a video recording.

13. The system as claimed in claim 11, wherein the individual playback device is an individual television receiver located at the second recording site.

14. The system as claimed in claim 11, wherein the first and the second hearing aid microphones are identical.

15. The system as claimed in claim 1, wherein the first and the second recordings are long-term spectral recordings.

16. The system as claimed in claim 11, wherein a dereverberation algorithm of the program for the second hearing aid device is individually parameterized based on the connection data.

17. The system as claimed in claim 11, wherein the connection data is directly inputted into the second hearing aid device via an interface.

18. The system as claimed in claim 1, the connection data is a quotient or a difference between the first and the second recordings.

19. The system as claimed in claim 1, wherein the data medium is played back in a predetermined individual environment that is different from the first recording site.

20. The system as claimed in claim 19, wherein the predetermined individual environment is a place where a wearer of the second hearing aid device usually listens to the playing back.

* * * * *